United States Patent
Cooper

(10) Patent No.: US 9,763,826 B2
(45) Date of Patent: Sep. 19, 2017

(54) GUIDE FOR AN EYE DROP DISPENSER BOTTLE FOR THE SELF-ADMINISTRATION OF EYE DROPS

(71) Applicant: Clifford Cooper, Loughton (GB)

(72) Inventor: Clifford Cooper, Loughton (GB)

( * ) Notice: Subject to any disclaimer, the term of this patent is extended or adjusted under 35 U.S.C. 154(b) by 0 days.

(21) Appl. No.: 14/759,290

(22) PCT Filed: Jan. 7, 2014

(86) PCT No.: PCT/GB2014/050039
§ 371 (c)(1),
(2) Date: Jul. 6, 2015

(87) PCT Pub. No.: WO2014/106759
PCT Pub. Date: Jul. 10, 2014

(65) Prior Publication Data
US 2015/0351960 A1    Dec. 10, 2015

(30) Foreign Application Priority Data

Jan. 7, 2013 (GB) .................................. 1300227.4
May 31, 2013 (GB) .................................. 1309804.1

(51) Int. Cl.
*A61F 9/00* (2006.01)

(52) U.S. Cl.
CPC .................................. *A61F 9/0026* (2013.01)

(58) Field of Classification Search
CPC ...... A61F 9/0008; A61F 9/0026; A61H 35/02
USPC ................ 604/294, 295, 300, 301, 302, 521
See application file for complete search history.

(56) References Cited

U.S. PATENT DOCUMENTS

| 3,439,674 | A |   | 4/1969  | Lelicoff |
|-----------|---|---|---------|----------|
| 4,002,168 | A |   | 1/1977  | Petterson |
| 4,085,750 | A | * | 4/1978  | Bosshold ............. A61F 9/0026 604/302 |
| 4,960,407 | A |   | 10/1990 | Cope |
| 5,064,420 | A | * | 11/1991 | Clarke ................. A61F 9/0026 604/295 |
| 5,221,027 | A | * | 6/1993  | Gibilsco ............... A61F 9/0026 222/420 |

(Continued)

FOREIGN PATENT DOCUMENTS

| CN | 202314375 | 7/2012 |
| CN | 202477946 | 10/2012 |

(Continued)

*Primary Examiner* — Imani Hayman
*Assistant Examiner* — James D Ponton
(74) *Attorney, Agent, or Firm* — Carmody Torrance Sandak & Hennessey LLP

(57) ABSTRACT

The guide (2) consists of a positioning member (16) that enables a user to align an eye drop dispenser bottle (4) with the eye to be treated. The guide (2) includes an attachment device (6) for removably attaching the guide (2) to the eye drop dispenser bottle (4) and two arms (14) connected to the attachment device (6) by a pair of multiple use living hinges (12). The positioning member (16) bridges the two arms (14) and is rotatable between a stowed position and an operational position, such that when in the operational position the positioning member (16) is arranged between the eye drop dispenser bottle (4) and the eye to be treated. The guide (2) further comprises a locking arrangement (18, 20) for locking the guide (2) in the operational position.

15 Claims, 4 Drawing Sheets

(56) References Cited

U.S. PATENT DOCUMENTS

| | | | |
|---|---|---|---|
| 5,607,410 A | 3/1997 | Branch | |
| 6,371,945 B1 * | 4/2002 | Sherman | A61F 9/0026 604/300 |
| 6,398,766 B1 | 6/2002 | Branch | |
| 6,508,793 B1 * | 1/2003 | Harrold | A61F 9/0008 604/294 |
| 8,216,195 B2 * | 7/2012 | Wu | A61F 9/0008 215/306 |
| 2005/0131358 A1 | 6/2005 | Skolik | |
| 2006/0157516 A1 | 7/2006 | Barber | |
| 2010/0174248 A1 | 7/2010 | Wu | |
| 2010/0286634 A1 | 11/2010 | Marx | |

FOREIGN PATENT DOCUMENTS

| | | |
|---|---|---|
| CN | 202637251 | 1/2013 |
| GB | 971137 | 9/1964 |
| GB | 1570171 | 6/1980 |
| WO | 2008/041177 | 4/2008 |

* cited by examiner

GUIDE FOR AN EYE DROP DISPENSER BOTTLE FOR THE SELF-ADMINISTRATION OF EYE DROPS

CROSS REFERENCE TO RELATED APPLICATIONS

This application is a National Stage of International Application No. PCT/GB2014/050039, filed Jan. 7, 2014, the subject matter of which is herein incorporated by reference in its entirety.

The present invention relates to a removable guide for positioning an eye drop dispenser relative to a user's eye during the administration of eye drops.

The self-administration of eye drops using gravity can be a difficult task not least because of the awkward position that a user has to adopt during the administration of eye drops. When applying eye drops, a user is required to tilt their head back and hold an eye drop dispenser directly above the eye to be treated. This position not only makes it difficult to apply eye drops accurately, which can result in the eye being missed all together in some instances, but can also lead to a loss of depth perception. The latter effect can make it difficult for some users to gauge exactly how far the eye drop dispenser is from the eye to be treated. These problems can result in a user losing confidence in their ability to self-administer eye drops.

A variety of guides that attempt to address these problems have been proposed. One such guide, in the form of a dispenser cap for an eye drop dispenser, is shown in US2010/0174248. The dispenser cap defines a cavity for enclosing the dispensing nozzle of the eye drop dispenser. The dispenser cap includes a holder that engages with the eye drop dispenser, along with a cap enclosure and an eyelid engaging member, both of which pivotally extend from the holder. During use, the eyelid engaging member is positioned on either the upper or lower section of the eyelid to pull the eyelid open and align the dispensing nozzle with the eye being treated. However the eyelid engaging member remains free to pivot about the holder during use. This means that the position of the dispensing nozzle can vary during use, which makes it difficult to maintain alignment between the dispensing nozzle and the eye being treated. Also, the fact that the eyelid engaging member is only positioned on either the upper or lower section of the eyelid means that the opposing section is free to move during the administration of eye drops, which can result in the user blinking during the administration of eye drops. These drawbacks mean that the guide is cumbersome to use when held in the awkward position described above.

Another such guide is shown in U.S. Pat. No. 4,960,407. This guide sits on the neck and shoulder region of an eye drop dispenser and includes an arm extending outwardly from the dispenser in the direction of the dispensing nozzle. A ring attached to the end of the arm remote from the eye drop dispenser is positioned around a user's eye during use to ensure alignment with the dispensing nozzle. The ring does not, however, function to hold the eyelids open. The guide comprises other components that allow it to rotate from an operational position, in which the ring is positioned downstream from the dispensing nozzle, to a stowed position where the ring is positioned below the eye drop dispenser. However the combination of the guide and eye drop dispenser when in the stowed position increases the overall dimensions when compared the eye drop dispenser alone, making it less practical to carry and use. Moreover, the guide is made from at least two separate components, which adds to its complexity and manufacturing costs.

The aim of the present invention is to overcome or substantially mitigate at least the problems outlined above.

According to a first aspect of the invention, there is provided a guide for delivering an eye drop solution from a dispenser bottle to a user's eye under gravity comprising an attachment device for detachable engagement with the dispenser bottle; two arms extending outwardly from the attachment device; a positioning member bridging the ends of the arms, the positioning member having a semi-circular profile; and, two living hinges connecting the attachment device to the arms at the ends remote from the positioning member, the living hinges being adapted to rotate the guide between a stowed position and an operational position repeatedly when the guide is attached to the dispenser bottle, such that when in the operational position the positioning member is located between the dispenser bottle and the user's eye so as to ensure alignment of the dispenser bottle with respect to the user's eye during the administration of the eye drop solution, the guide further comprises a first locking arrangement for locking the guide in the operational position thereby ensuring that the distance between the user's eye and the dispenser bottle is fixed during the administration of the eye drop solution. The fact the attachment means can be removably attached to the dispenser bottle means that the guide can be reused on other dispenser bottles.

Preferably, the positioning member is arranged to be resiliently deformable under manual pressure so that the distance of the opening in the semi-circular profile (i.e. the distance between opposing ends of the semi-circular profile) can be increased or decreased. If necessary, the distance of the opening in the semi-circular profile of the positioning member can be decreased up to the extent that the opening closes. The distance of the opening in the semi-circular profile of the positioning member can be decreased by at least substantially 2 mm or preferably 5 mm. The fact that the positioning means is resiliently deformable means that the positioning means can automatically return to its biased state following deformation. In use, this action is beneficially used to apply a light pressure to the upper and lower eyelids to gently prise and hold them open so as to increase the exposed surface area of the eye being treated. Moreover, the fact that the eyelids are held open by the positioning means prevents the user from blinking during the application of eye drops.

Preferably, the first locking arrangement a first pair of lugs extending from the attachment means and a second pair of lugs extending from the two arms, wherein the first pair of lugs comprise holes arranged to receive respective protrusions on the second pair of lugs in an interference fit when the guide is in the operational position. The first locking arrangement is adapted to disengage when the guide is rotated under manual pressure from the operational position. Preferably, the second pair of lugs are arranged to contact the attachment member when the guide is in the operational position so as to prevent the guide from rotating past the operational position. The fact that the second pair of lugs are arranged to contact the attachment means not only helps to keep the guide in the operational position but also prevent the guide from being forced past the operational position, which could damage the living hinges.

The guide may further comprise a second locking arrangement for locking the guide in the stowed position. The second locking arrangement comprises engaging or clipping the positioning member around the body of the dispenser bottle in an interference fit. Preferably, the second locking member is adapted to disengage when the guide is rotated under manual pressure from the stowed position. This arrangement ensures that the overall dimensions of the combination of the guide and the dispenser bottle remains compact, which make it practical to carry and use.

Preferably, the attachment means further comprises a wall arranged to contact the dispenser bottle when the guide is attached to the dispenser bottle. The wall is adapted to engage the dispenser bottle so as to stabilise the guide during the administration of eye drops by ensuring that the attachment member remains substantially aligned with the horizontal plane of the dispenser bottle.

Preferably, the arms and the positioning member are arranged to rotate about the attachment device through substantially 180 degrees between the stowed position and the operational position, and the end surface of the positioning member comprises a plurality of coarse areas. The presence of coarse areas on the end surface of the positioning member improves the gripping force of the guide on the eyelids which, in turn, reduces the pressure that is required to be applied by the guide.

Preferably, the attachment device comprises an open collar resiliently deformable under manual pressure. This allows the attachment device to be easily and conveniently clipped on and secured around the neck of the dispenser bottle.

Preferably, the guide is formed as a unitary structure. The fact that the guide is made as a single piece makes it more robust than other guides that comprise two or more components. It also reduces the overall complexity of the guide and minimises manufacturing costs.

According to a second aspect of the invention, there is provided a method of using the guide when attached to a dispenser bottle, the method comprising the steps of: i) rotating the guide to an operational position; ii) compressing the ends of the positioning member to reduce the opening in the semi-circular profile of the positioning member; iii) inverting the dispenser bottle; iv) aligning the dispenser bottle with the eye to be treated by placing the positioning member around the eye so that it extends across the upper and lower eyelids; v) releasing the ends of the positioning member so as to prise and hold the eyelids open, and prevent blinking during the administration of eye drops; and, vi) compressing the body of the dispenser bottle to induce drops to fall from a dispensing nozzle onto the user's eye.

These and other aspects of the invention will now be described, by way of example only, with reference to the accompanying drawings, in which.

In the drawings, like parts are denoted by like reference numerals.

Figure 1:
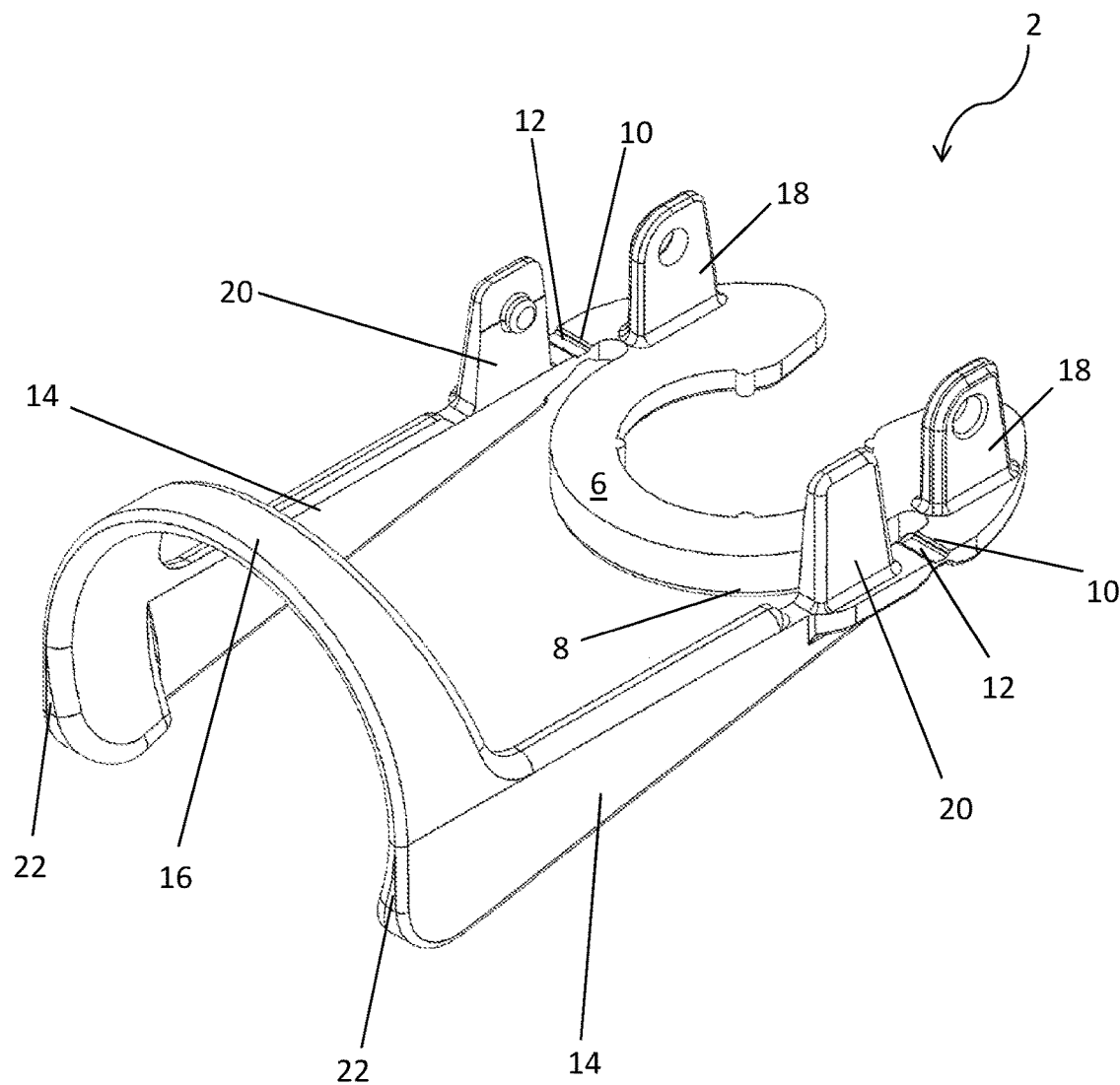
FIG. 1 is a perspective view of a guide for an eye drop dispenser in accordance with the invention.
Figure 2:
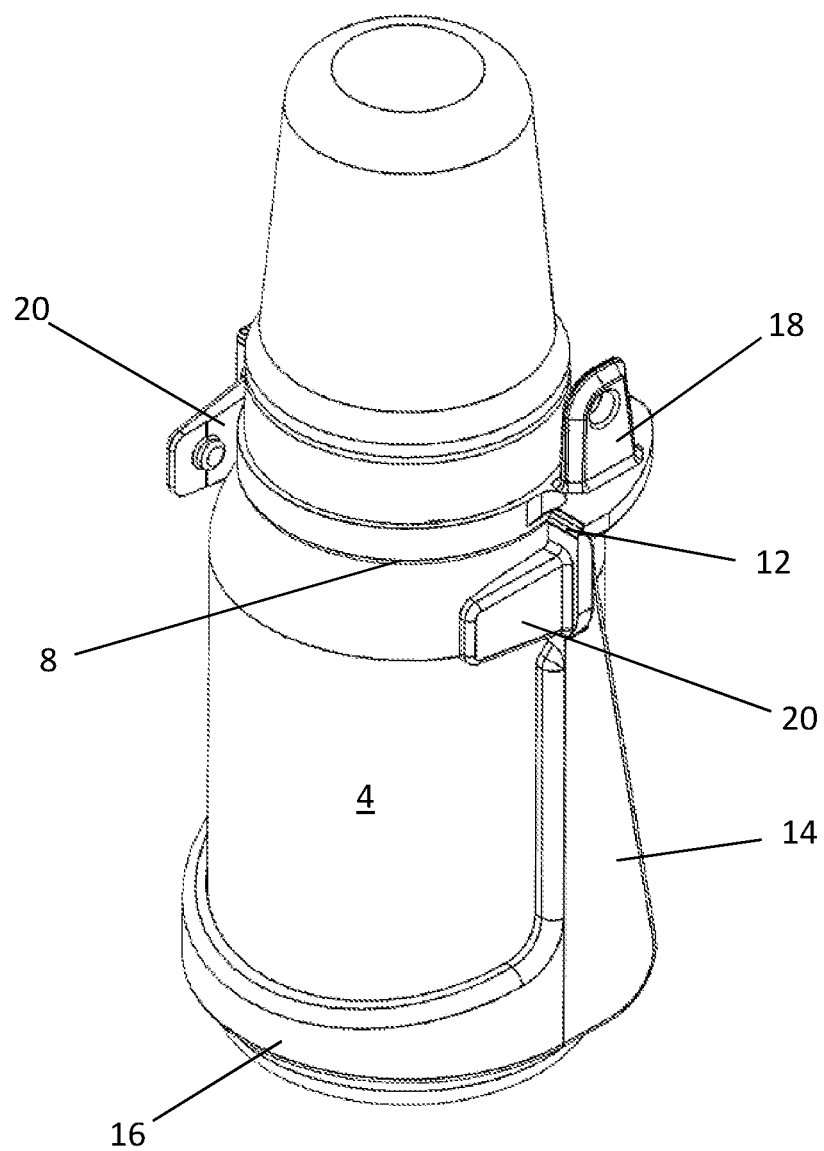
FIG. 2 is a perspective view of the guide of FIG. 1 removably attached to the eye drop dispenser in a stowed position.

FIG. 1 shows a guide 2 for an eye drop dispenser in accordance with the invention. The various features of the guide are beneficially arranged to facilitate the application of an eye drop solution in an easily controlled, fast, safe, and repeatable manner. The guide 2 comprises an attachment device in the form of an open collar 6 (hereinafter "the collar"), which is used to clip the guide 2 onto an eye drop dispenser 4 (hereinafter "the dispenser"). With reference to FIG. 2, the collar 6 is adapted to be resiliently deformable under manual pressure, which enables it to be pushed over and removably secured to the neck region of the dispenser 4. The opening in the collar 6 is outwardly tapered to facilitate the correct positioning of the guide 2 before the collar 6 is pushed over the neck of the dispenser 4. A wall 8 extends downwardly from the outer circumference of the collar 6 and is arranged to sit on the shoulder of the dispenser 4. The wall 8 is adapted, in combination with the shoulder of the dispenser 4, to stabilise the guide 2 during the administration of eye drops by ensuring that the collar 6 remains substantially aligned with the horizontal plane of the dispenser 4. The inner circumference of the collar 6 comprises a plurality of inwardly projecting teeth for engaging the neck of the dispenser 4. Alternatively, the inner circumference of the collar 6 can be smooth.

The collar 6 further comprises two end regions 10 that are radially opposite each other. Two hinged sections 12, in the form of multiple use living hinges, are secured at one end to respective end regions 10. That is, the hinged sections 12 are thin flexible hinges made from the same material as the rest of the guide 2. The use of living hinges is beneficial because it minimises the complexity of the guide 2 and ensures that the guide 2 can be manufactured as a single piece. That is, the guide 2 is formed as a unitary structure. The fact that the guide 2 is made as a single piece makes it more robust than other guides that comprise two or more parts.

The guide 2 further comprises two arms 14 integrally form with and secured to the other end of respective hinged sections 12. The arms 14 extend downwardly from their respective hinged sections 12 either side of the dispenser 4 when the guide 2 is attached to the dispenser 4. A positioning member in the form of a bridging section 16 having a substantially semi-circular profile contoured to fit an eye connects the ends of the arms 14 remote from the hinged sections 12. The arms 14 and the bridging section 16 are resiliently deformable under manual pressure so as to increase or reduce the gap in the semi-circular profile of the bridging section 16. This enables the bridging section 16 to be pushed over the body of the dispenser 4 and substantially locked into a stowed position as shown in FIG. 2. When in the stowed position, the inner surface of the bridging section 16 is arranged to substantially conform with and extend around a significant proportion of the circumference of the body of the dispenser 4. More specifically, the inner surface of the bridging section 16 extends around approximately two thirds of the circumference of the body of the dispenser 4. This arrangement allows the guide 2 to be snapped onto and securely held in the stowed position around the body of the dispenser 4. With the guide 2 in the stowed position, the overall dimensions of the dispenser 4 and guide 2 remain largely the same as those of the dispenser 4 alone.

Figure 3:
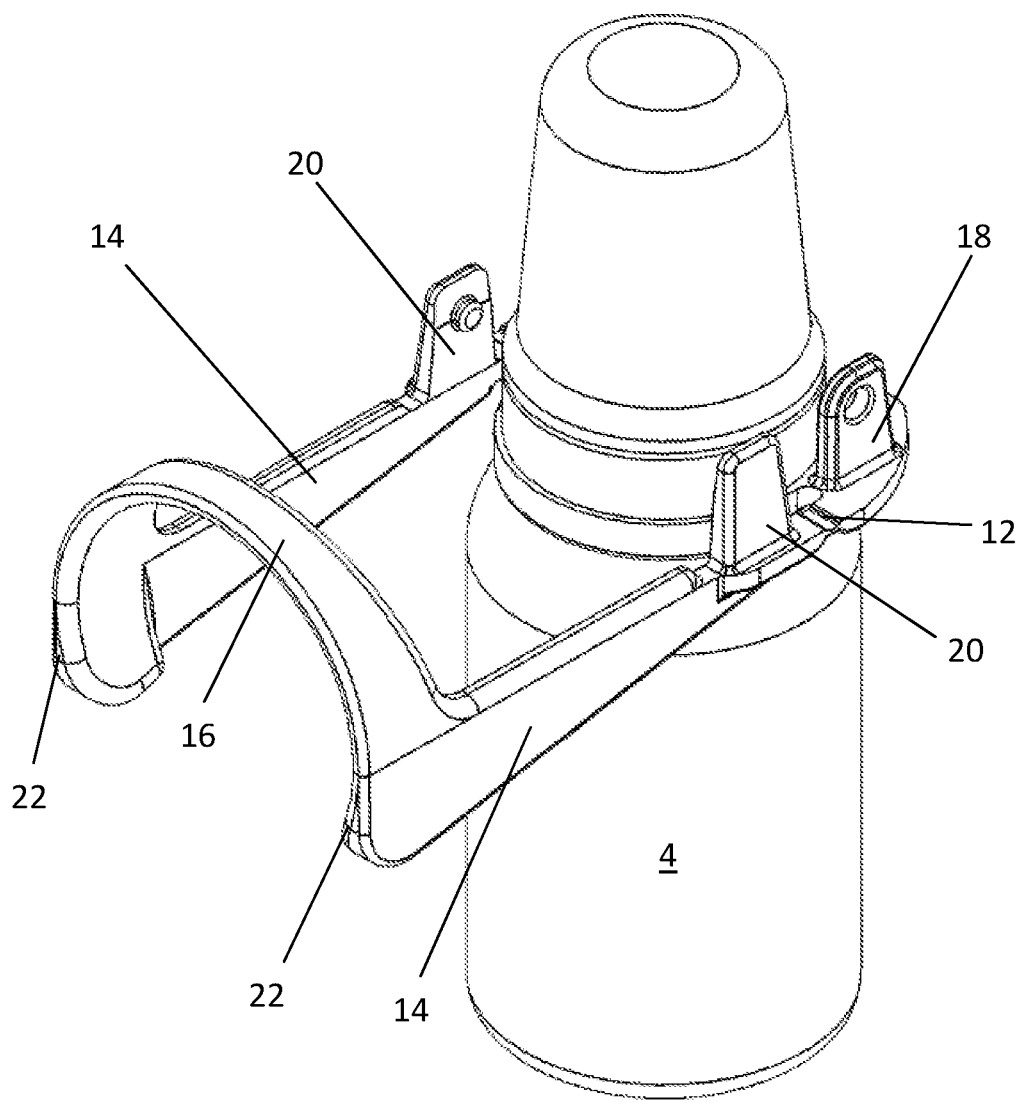
FIG. 3 is a perspective view of the guide of FIG. 1 removably attached to the eye drop dispenser midway between the stowed position and an operational position; and, FIG. 4 is a perspective view of the guide of FIG. 1 removably attached to the eye drop dispenser in the operational position.
Figure 4:
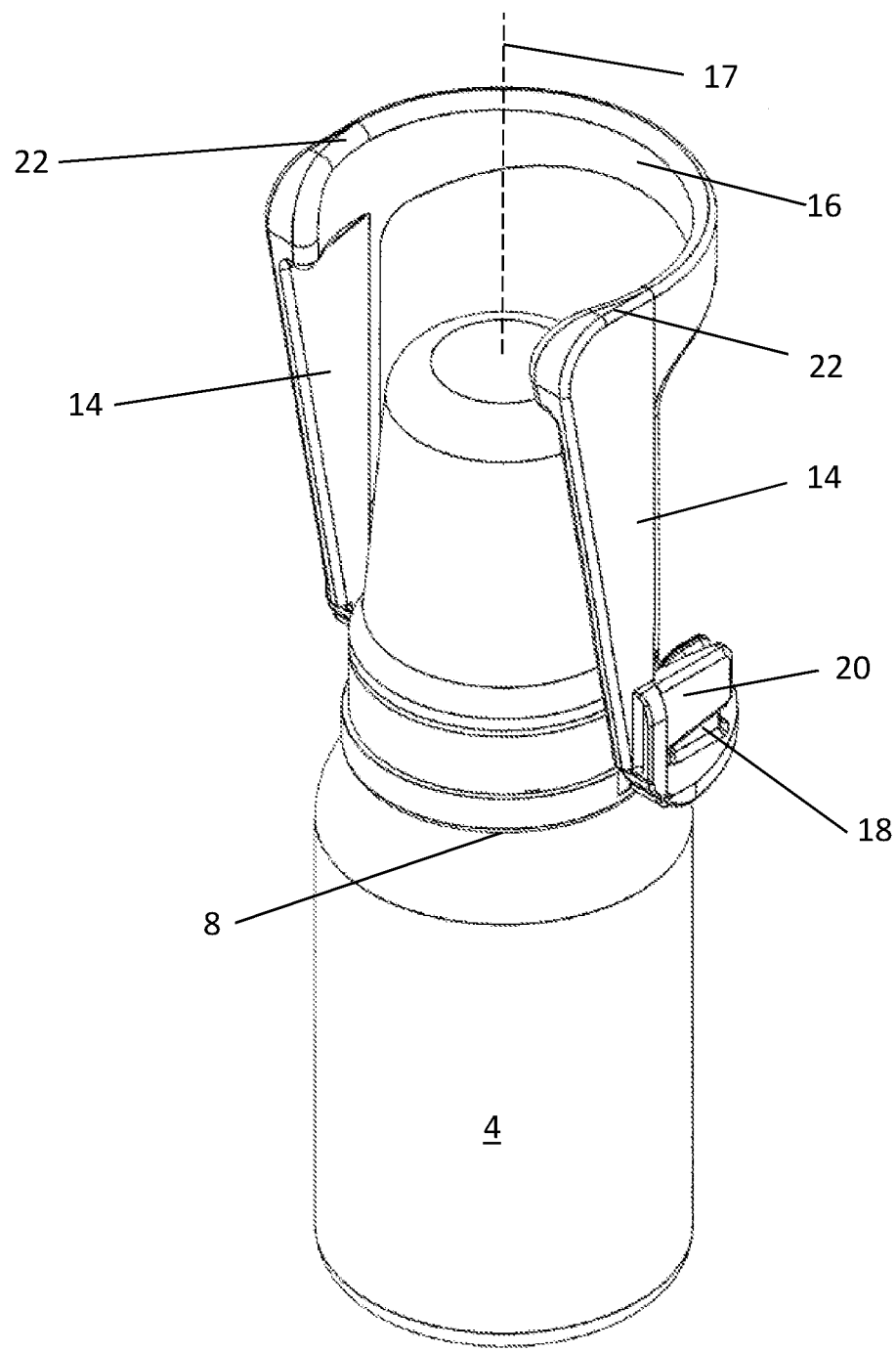

The hinged sections 12 act as pivots to effect substantially 180 degree rotational movement of the arms 14 and the bridging section 16 about the collar 6 between the stowed position, as shown in FIG. 2, and an operational position as shown in FIG. 4. FIG. 3 shows the guide 2 positioned midway between the stowed position and the operational position. In the operational position, the bridging section 16 of the guide 2 is located above the dispenser 4 and intersects the eye solution delivery line 17 of the dispensing nozzle (not shown). The bridging section 16 is used to align or position the dispenser 4 with respect the eye to be treated when the guide 2 is in the operational position. The end surface of the bridging section 16 comprises a plurality of areas 22 having a coarse surface finish when compared to the surface finish of the rest of the guide 2. A first pair of lugs 18 extends from the upper surface of the collar 6. A second pair of lugs 20 protrudes from the arms 14 near the hinged sections 12. The first pair of lugs 18 comprise holes that are arranged to receive respective protrusions on the second pair of lugs 20 when the guide 2 is in the operational position. This provides a locking arrangement that substantially locks the guide 2 in the operational position. As a result, the distance between the bridging section 16 and the dispensing nozzle of the dispenser 4 remains fixed during the administration of eye drops. This locking arrangement can be overcome by moving the guide 2 under manual pressure from the operational position. Alternative means for locking the guide 2 in the operational position are also envisaged. For example, the guide 2 could use a rack and pawl combination or the like. Alternatively the hinged sections 12 may comprise living hinges that adapted to substantially lock the guide 2 in position when the guide 2 is rotated into the operational position. The second pair of lugs 20 may be modified to engage the upper surface of the collar 6 when the guide 2 is in the operational position so as to prevent the guide 2 from being forced past the operational position.

In use, a user rotates the guide 2 from the stowed position to the operational position. The user then squeezes the ends of the resiliently deformable bridging section 16 to reduce the gap in the semi-circular profile of bridging section 16. The bridging section 16 can be deformed in this manner up to the extent that the gap in the semi-circular profile of bridging section 16 closes. The user then inverts the dispenser 4 and places the bridging section 16 of the guide 2 around the eye so that it extends across both the upper and lower eyelids. The user, while holding the bridging section 16 against the upper and lower eyelids, then releases the ends of the bridging section 16. As a result, the bridging section 16 automatically returns back to its biased state. That is, the bridging section 16 automatically returns to its original dimensions, which include a gap in the semi-circular profile of the bridging section 16 of substantially 2 cm. This has the effect of applying a light pressure to the upper and lower eyelids to gently prise and hold them open, thereby increasing the exposed surface area of the eye that would have otherwise been exposed had the bridging section 16 not been resiliently deformable. The fact that the bridging section 16 holds the eyelids open removes the need for the user, or anyone else, to use their fingers to hold the eyelids open, which is not always hygienic. The presence of the coarse areas 22 at the end surface of the bridging section 16 improves the gripping force acting on the eyelids by the guide 2. This means that the pressure applied to the eyelids by the guide 2 can be minimised. Moreover, the fact that the bridging section is held against both the upper and lower eyelids during use prevents the user from blinking during the administration of eye drops. Using the guide 2 ensures that the dispenser 4 is positioned correctly with respect to the user's eye. As a result, the dispensing nozzle can be aligned with the user's eye in a repeatable manner and at a predetermined distance from the eye, thereby minimising the time that the user is required to adopt the awkward position outlined above. The dispenser 4 may then be squeezed to induce drops to fall from the dispensing nozzle onto the user's eye.

Various modifications will be apparent to those skilled in the art. For example, in an alternative embodiment, the collar 6 of the guide 2 may be a closed collar instead of the open collar as described above. Such a collar can be removably secured around the neck of the dispenser 4 only after the cap of the dispenser 4 has been removed. The collar 6 can then be placed over and secured around the neck of the dispenser 4. Alternatively the guide 2 could be moulded to the dispenser 4 itself.

I claim:

1. A guide for delivering an eye drop solution from a dispenser bottle to a user's eye, the guide comprising:
   an attachment device for removably attaching the guide to the dispenser bottle;
   two arms extending outwardly from the attachment device, each arm comprising an elongated section having opposing first and second ends;
   a positioning member bridging between the first ends of the arms, the positioning member having a semi-circular profile;
   two hinges connecting the attachment device to the second ends of the arms, the hinges being adapted to rotate the guide between a stowed position and an operational position repeatedly when the guide is attached to the dispenser bottle, such that when in the operational position the positioning member is arranged between the dispenser bottle and the user's eye; and
   a first locking arrangement for locking the guide in the operational position in which eye drop solution is delivered to a user's eye under gravity from the dispenser bottle to which the guide is attached during use, the first locking arrangement comprising first and second pairs of lugs with the first pair of lugs extending from the attachment device and the second pair of lugs extending from the two arms, wherein each lug of the second pair of lugs includes a protrusion and wherein each lug of the first pair of lugs includes a hole arranged to receive one of the protrusions, whereby in the operational position each lug of the first pair of lugs engages with a respective lug of the second pair of lugs in an interference fit, and
   wherein the two hinges are flexible sections of the guide and integrally formed with the arms and the attachment device, each flexible section being a living hinge.

2. The guide according to claim 1, wherein opposing ends of the semi-circular profile of the positioning member are separated by a distance corresponding to a diameter of the semi-circular profile and wherein the positioning member is resiliently deformable under manual pressure so as to increase or decrease the distance between the opposing ends of the semi-circular profile.

3. The guide according to claim 2, wherein the distance between the opposing ends of the semi-circular profile of the positioning member can be decreased so that the opposing ends of the semi-circular profile touch one another.

4. The guide according to claim 2, wherein the distance between the opposing ends of the semi-circular profile of the positioning member can be decreased by at least substantially 2 mm.

5. The guide according to claim 2, wherein the distance between the opposing ends of the semi-circular profile of the positioning member can be decreased by 5 mm.

6. The guide according to claim 1, wherein the first pair of lugs and the second pair of lugs are adapted to disengage when the guide is rotated under manual pressure from the operational position.

7. The guide according to claim 1, wherein the second pair of lugs are arranged to contact the attachment device when the guide is in the operational position to prevent the guide from rotating past the operational position.

8. The guide according to claim 1, further comprising a second locking arrangement for locking the guide in the stowed position when the guide is attached to the dispenser bottle.

9. The guide according to claim 8, wherein the positioning member is the second locking arrangement and is adapted to form an interference fit with the dispenser bottle.

10. The guide according to claim 8, wherein the positioning member is adapted to disengage from the dispenser bottle when the guide is rotated under manual pressure from the stowed position.

11. The guide according to claim 1, wherein the attachment device further comprises a wall arranged to contact the dispenser bottle when the guide is attached to the dispenser bottle.

12. The guide according to claim 1, wherein the arms and the positioning member are arranged to rotate about the attachment device through substantially 180 degrees between the stowed position and the operational position.

13. The guide according to claim 1, wherein the attachment device comprises an open collar resiliently deformable under manual pressure.

14. The guide according to claim 1, wherein a surface of the positioning member comprises a plurality of coarse areas.

15. A guide for delivering an eye drop solution from a dispenser bottle to a user's eye, the guide comprising:
   an attachment device for removably attaching the guide to the dispenser bottle;
   two arms extending outwardly from the attachment device, each arm comprising an elongated section having opposing first and second ends;
   a positioning member bridging between the first ends of the arms, the positioning member having a semi-circular profile;
   two hinges connecting the attachment device to the second ends of the arms, the hinges being adapted to rotate the guide between a stowed position and an operational position repeatedly when the guide is attached to the dispenser bottle, such that when in the operational position the positioning member is arranged between the dispenser bottle and the user's eye; and
   a first locking arrangement for locking the guide in the operational position in which eye drop solution is delivered to a user's eye under gravity from the dispenser bottle to which the guide is attached during use, the first locking arrangement comprising first and second pairs of lugs with the first pair of lugs extending from the attachment device and the second pair of lugs extending from the two arms, wherein in the operational position each lug of the first pair of lugs engages with a respective lug of the second pair of lugs in an interference fit, and
   wherein the two hinges are flexible sections of the guide and are integrally formed with the arms and the attachment device, each flexible section being a living hinge.

* * * * *